United States Patent
Bristow

(10) Patent No.: US 10,004,231 B2
(45) Date of Patent: Jun. 26, 2018

(54) METHOD OF INCREASING YIELD BY TREATING WITH FUNGICIDAL COMPOSITIONS

(71) Applicant: ROTAM AGROCHEM INTERNATIONAL COMPANY LIMITED, Chai Wan (HK)

(72) Inventor: James Timothy Bristow, Chai Wan (HK)

(73) Assignee: Rotam Agrochem International Company Limited, Chai Wan (HK)

( * ) Notice: Subject to any disclaimer, the term of this patent is extended or adjusted under 35 U.S.C. 154(b) by 0 days. days.

(21) Appl. No.: 15/032,596

(22) PCT Filed: Sep. 9, 2014

(86) PCT No.: PCT/CN2014/086123
§ 371 (c)(1),
(2) Date: Apr. 27, 2016

(87) PCT Pub. No.: WO2015/062358
PCT Pub. Date: May 7, 2015

(65) Prior Publication Data
US 2016/0249616 A1 Sep. 1, 2016

(30) Foreign Application Priority Data

Oct. 30, 2013 (BR) .......................... 1020130279773

(51) Int. Cl.
| | | |
|---|---|---|
| *A01N 43/653* | (2006.01) | |
| *A01N 43/40* | (2006.01) | |
| *A01N 43/54* | (2006.01) | |
| *A01N 47/24* | (2006.01) | |
| *A01N 43/56* | (2006.01) | |

(52) U.S. Cl.
CPC ........... *A01N 43/653* (2013.01); *A01N 43/40* (2013.01); *A01N 43/54* (2013.01); *A01N 43/56* (2013.01); *A01N 47/24* (2013.01)

(58) Field of Classification Search
None
See application file for complete search history.

(56) References Cited

U.S. PATENT DOCUMENTS

| | | |
|---|---|---|
| 2005/0101639 A1 | 5/2005 | Ammermann et al. |
| 2015/0313226 A1 | 11/2015 | Ammermann et al. |
| 2015/0313227 A1 | 11/2015 | Ammermann et al. |
| 2016/0143282 A2 | 5/2016 | Ammermann et al. |

FOREIGN PATENT DOCUMENTS

| | | | |
|---|---|---|---|
| BR | 201103462 | 7/2013 | |
| CN | 1561732 | 1/2005 | |
| CN | 101637157 | 2/2010 | |
| CN | 101715771 | 6/2010 | |
| CN | 101779656 | 7/2010 | |
| CN | 102047889 | 5/2011 | |
| CN | 102047890 | 5/2011 | |
| CN | 102057916 | 5/2011 | |
| CN | 102960347 | 3/2013 | |
| CN | 103081942 | 5/2013 | |
| WO | 02073852 | 9/2003 | |
| WO | 03073852 A2 | 9/2003 | |
| WO | 2010078852 | 7/2010 | |
| WO | WO 2010078852 A1 * | 7/2010 | ............. A01N 37/50 |
| WO | 2011006603 | 1/2011 | |
| WO | 2011095134 | 8/2011 | |
| WO | 2012040804 | 4/2012 | |
| WO | 2012106785 | 8/2012 | |

OTHER PUBLICATIONS

"Efficacy Evaluation of Pesticides Registed in Recent Two Years in Fields" Pesticide Market News, No. No. 8, Apr. 30, 2009 (Apr. 30, 2009), ISSN: pp. 36-37, 50 (with translation).
Li, Haiping. "Developing Progress and Trends of Fungicides Novel Varieties of the World from the 1980s" Pesticide Science and Administration, vol. vol. 25, No. No. 10, Dec. 31, 2004 (Dec. 31, 2004), ISSN: pp. 22-28, 32.
"Efficacy Evaluation of Pesticides Registed in Recent Two Years in Fields" Pesticide Market News, No. No. 8, Apr. 30, 2009 (Apr. 30, 2009), ISSN: pp. 36-37, 50.
Song, Ruili et al. "Control Efficacy of SYP-1620 against Sunflower Rust" Agrochemicals, vol. vol. 47, No. No. 12, Dec. 31, 2008 (Dec. 31, 2008), ISSN: pp. 871-873.
Vincelli, P. 2002. Qol (Strobilurin) Fungicides: Benefits and Risks. The Plant Health Instructor. DOI: 10.1094/PHI-I-2002-0809-02. Updated, 2012.
International Search Report (PCT/CN2014/086123) dated Dec. 12, 2014.

* cited by examiner

*Primary Examiner* — Heidi Reese
(74) *Attorney, Agent, or Firm* — Dickinson Wright PLLC

(57) ABSTRACT

A method of increasing the yield of a plant is provided. The method involves applying plants or surrounding with a composition that includes components (A) strobilurin fungicides and (B) triazole fungicides, which has the capacity to improve the yield of the plant.

18 Claims, No Drawings

METHOD OF INCREASING YIELD BY TREATING WITH FUNGICIDAL COMPOSITIONS

This application is a 371 national phase entry of PCT/CN2014/086123, filed 9 Sep. 2014, which claims benefit of BR Patent Application No. 10 2013 027977.3, filed Oct. 30, 2013, the entire contents of which are incorporated herein by reference for all purposes.

FIELD OF THE INVENTION

The present invention relates to a method of increasing the yield of a plant by applying the plant or surrounding with a composition that includes components (A) strobilurin fungicides and (B) triazole fungicides and, which has the capacity to improve the yield of the plant.

BACKGROUND

Fungal diseases represent a major threat to economically important agricultural crops. The yield of plants, for example, cotton, coffee, sugar cane, sunflower, corn, soybean and wheat, are adversely impacted by fungal diseases. Soybean rust is one of the fungal diseases caused by *Phakopsora pachyrhizi*. Soybean rust has been known to drastically reduce yields. Yield loss up to 80% has been reported. It could have a major impact on both total soybean production and production costs. *Alternaria* is also one of the fungal diseases caused by *Alternaria* species. *Alternaria* causes significant yield losses of sunflower in hot and humid areas. Yield loss up to 90% has been reported in subtropical areas. Therefore, there is a continuing need to provide a fungal composition for controlling fungal pathogens, thereby increasing the yield of plant.

Strobilurin or strobilurin-type fungicides are a well-known class of fungicides with a broad spectrum of disease control. They are extracted from the fungus *Strobilurus tenacellus*. They have a suppressive effect on other fungi, reducing competition for nutrients; they inhibit electron transfer between cytochrome b and cytochrome $C_1$ at the ubiquinol oxidising site in mitochondria, disrupting metabolism and preventing growth of the target fungi. Examples of strobilurins are fluoxastrobin, mandestrobin, azoxystrobin, bifujunzhi, coumoxystrobin, enoxastrobin, flufenoxystrobin, jiaxiangjunzhi, picoxystrobin, pyraoxystrobin, pyraclostrobin, pyrametostrobin, triclopyricarb, dimoxystrobin, fenaminstrobin, metominostrobin, orysastrobin, kresoxim-methyl, trifloxystrobin, famoxadone and fenamidone.

Triazoles are a class of systemic fungicides that enter the plant and spread from the site of application to untreated or newly grown area, uprooting existing fungi or protecting the plant from future attacks. The mechanism of action of these fungicides is due to their ability to interfere with the biosynthesis of biosteroids or to inhibit the biosynthesis of ergosterol. Ergosterol is needed for membrane structure and function. It is essential for the development of functional cell walls by fungi. Therefore, application of triazoles results in abnormal fungal growth and eventually death. Examples of triazoles are azaconazole, bromuconazole, cyproconazole, diclobutrazol, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole, ipconazole, metconazole, myclobutanil, penconazole, propiconazole, prothioconazole, quinconazole, simeconazole, tebuconazole, tetraconazole, triadimefon, triadimenol, triticonazole, uniconazole, amitrol, bitertanol, climbazole, clotrimazole, fluotrimazole, paclobutrazol, triazbutil and 1-(4-fluorophenyl)-2-(1H-1,2,4-triazole-1-yl)ethanone.

However, experience with the strobilurin fungicides worldwide indicates there is a high risk of development of resistant pathogen subpopulations. Resistance has been reported worldwide in an increasing number of pathogens of field crops, fruit, vegetable, and so on (Vincelli, P. 2002. $Q_oI$ (Strobilurin) Fungicides: Benefits and Risks. *The Plant Health Instructor*. DOI: 10.1094/PHI-I-2002-0809-02. Updated, 2012). As suggested in Vincelli, P. 2002, mixing the strobilurin fungicides with other fungicides can reduce selection pressure towards resistance.

Therefore, it would be advantageous to provide a method of increasing the yield of a plant by applying a plant which is susceptible to fungal diseases caused by fungal pathogens or surrounding.

SUMMARY

One aspect of the present invention relates to a method of increasing the yield of a plant by applying the plant which is susceptible to fungal diseases caused by fungal pathogens or surrounding with a composition that includes components (A) strobilurin fungicides and (B) triazole fungicides, which has the capacity to improve the yield of the plant.

Another aspect of the present invention thus provides a method of increasing the yield of a plant comprising steps:
 (1) applying a plant or surrounding with an effective amount of a composition comprising components (A) at least one strobilurin fungicide, and (B) at least one triazole fungicide; and
 (2) growing the plant to increase the yield of the plant.

The invention also relates to a plant treated with a composition hereinbefore defined, either before infestation by a fungus or treated to combat an existing fungal infection.

DETAILED DESCRIPTION

"Increasing the yield" or "increase the yield" refers to a measurable amount of the increased yield of the plant over the yield of the same plant under the same condition, but without the application of the method according to embodiments of the present invention. The yield can be increased by at least about 0.5%, 1%, 2%, 4%, 10%, 20%, 50%, 75%, 100%, 150% or 200%. The yield can be measured by means of, but not limit to, the yield of a product; plant weight; fresh weight of plant or any parts of the plant; dry weight of plant or any parts of the plant; specific ingredients of the plant including, without limitation, sugar content, starch content, oil content, protein content, vitamin content; leaf area; stem volume; plant height or any methods which apparent to the person skilled in the art. In some embodiments, the yield is increased at least about 0.5%. In other embodiments, the yield is increased at least about 1%. In some embodiments, the yield is increased at least about 2%. In certain embodiments, the yield is increased at least about 50%.

The word "surrounding" refers to the place on which the plants are growing, the place on which the plant propagation materials of the plants are sown or the place on which the plant propagation materials of the plants will be sown.

It has been surprisingly found that there is an increase of the yields of plants which are susceptible to fungal diseases caused by fungal pathogens, after applying the composition according to embodiments of the present invention. Particularly preferred plants are cotton, coffee, sugar cane, sunflower, corn, soybean and wheat.

The yield increase achieved by applying the composition according to according to embodiments of the invention is higher than the yield without applying the composition. Moreover, the increase of yield achieved by applying the composition according to according to embodiments of the invention has been found to be even higher as compared to the yield obtained by applying the individual components, i.e., single strobilurin fungicide or single triazole fungicide, each.

Accordingly, embodiments of this invention provides a method of increasing the yield of a plant, in particular cotton, coffee, sugar cane, sunflower, corn, soybean and wheat. The method comprises treating a site, for example a plant, one or more parts thereof (such as leaves or seeds), with the components (A) at least one strobilurin fungicide and (B) at least one triazole fungicide. The components (A) and (B) may be applied in any desired sequence, any combination, consecutively or simultaneously.

The component (A) strobilurin fungicides may be present in the composition in any suitable amount, and is generally present in an amount of from 1% to 75% by weight of the composition, preferably from 1% to 50% by weight of the composition, more preferably from 3% to 30% by weight of the composition.

The component (A) strobilurin fungicides may be any fungicidally active strobilurin compounds, for example with such compounds being known in the art and commercially available. The strobilurin compound is preferably one or more selected from fluoxastrobin, mandestrobin, azoxystrobin, bifujunzhi, coumoxystrobin, enoxastrobin, flufenoxystrobin, jiaxiangjunzhi, picoxystrobin, pyraoxystrobin, pyraclostrobin, pyrametostrobin, triclopyricarb, dimoxystrobin, fenaminstrobin, metominostrobin, orysastrobin, kresoxim-methyl, trifloxystrobin, famoxadone and fenamidone. In some embodiments, the strobilurin fungicide is selected from the group consisting of azoxystrobin, picoxystrobin, pyraclostrobin and combinations thereof. In certain embodiments, the strobilurin fungicide is azoxystrobin.

The component (B) triazole fungicides may be present in the composition in any suitable amount, and is generally present in an amount of from 1% to 70% by weight of the composition, preferably from 2% to 50% by weight of the composition, more preferably from 5% to 25% by weight of the composition.

The component (B) triazole fungicides may be any fungicidally active triazole compounds, for example with such compounds being known in the art and available commercially. The triazole compound is preferably one or more selected from azaconazole, bromuconazole, cyproconazole, diclobutrazol, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole, ipconazole, metconazole, myclobutanil, penconazole, propiconazole, prothioconazole, quinconazole, simeconazole, tebuconazole, tetraconazole, triadimefon, triadimenol, triticonazole, uniconazole, amitrol, bitertanol, climbazole, clotrimazole, fluotrimazole, paclobutrazol, triazbutil and 1-(4-fluorophenyl)-2-(1H-1,2,4-triazole-1-yl)ethanone. In some embodiments, the triazole fungicide is selected from the group consisting of azaconazole, cyproconazole, difenoconazole, flutriafol, metconazole, propiconazole, tebuconazole and combinations thereof. In certain embodiments, the triazole fungicide is cyproconazole, flutriafol or tebuconazole.

The components (A) and (B) may be present in the composition or applied in any amounts relative to each other, to provide the enhanced or synergistic effect of the mixture.

In particular, the weight ratio of the components (A) and (B) in the composition independently is preferably in the range of from 25:1 to 1:25, 20:1 to 1:20, or 15:1 to 1:15, more preferably 10:1 to 1:10, 5:1 to 1:5 or 2.5:1 to 1:2.5. In some embodiments, the weight ratio of the components (A) and (B) in the composition independently is 2.5:1. In certain embodiments, the weight ratio of the components (A) and (B) in the composition independently is 1:2.5.

In a preferred embodiment, each combination is a composition comprising, components (A) and (B), and optionally one or more auxiliaries. The auxiliaries employed in the composition will depend upon the type of formulation and/or the manner in which the formulation is to be applied by the end user. Formulations incorporating the composition according to embodiments of the present invention are described hereinafter. Suitable auxiliaries which may be comprised in the composition according to according to embodiments of the invention are all customary formulation adjuvants or components, such as extender, carriers, solvents, surfactants, stabilizers, anti-foaming agents, anti-freezing agents, preservatives, antioxidants, colorants, thickeners, solid adherents and inert fillers. Such auxiliaries are known in the art and are commercially available. Their use in the formulation of the compositions will be apparent to the person skilled in the art.

The fungicidal composition may further comprise one or more inert fillers. Such inert fillers are known in the art and available commercially. Suitable fillers include, for example, natural ground minerals, such as kaolins, aluminas, talc, chalk, quartz, attapulgite, montmorillonite, and diatomaceous earth, or synthetic ground minerals, such as highly dispersed silicic acid, aluminum oxide, silicates, and calcium phosphates and calcium hydrogen phosphates. Suitable inert fillers for granules include, for example, crushed and fractionated natural minerals, such as calcite, marble, pumice, sepiolite, and dolomite, or synthetic granules of inorganic and organic ground materials, as well as granules of organic material, such as sawdust, coconut husks, corn cobs, and tobacco stalks.

The fungicidal composition optionally includes one or more surfactants which are preferably non-ionic, cationic and/or anionic in nature and surfactant mixtures which have good emulsifying, dispersing and wetting properties, depending on the nature of the active compound to be formulated. Suitable surfactants are known in the art and are commercially available. Suitable anionic surfactants can be both so-called water-soluble soaps and water-soluble synthetic surface-active compounds. Soaps which may be used are the alkali metal, alkaline earth metal or substituted or unsubstituted ammonium salts of higher fatty acid ($C_{10}$-$C_{22}$), for example the sodium or potassium salt of oleic or stearic acid, or of natural fatty acid mixtures. The surfactant can be an emulsifier, dispersant or wetting agent of ionic or nonionic type. Examples which may be used are salts of polyacrylic acids, salts of lignosulphonic acid, salts of phenylsulphonic or naphthalenesulphonic acids, polycondensates of ethylene oxide with fatty alcohols or with fatty acids or with fatty amines, substituted phenols, especially alkylphenols, sulphosuccinic ester salts, taurine derivatives, especially alkyltaurates, or phosphoric esters of polyethoxylated phenols or alcohols. The presence of at least one surfactant is generally required when the active compound and/or the inert carrier and/or auxiliary/adjuvant are insoluble in water and the vehicle for the final application of the composition is water.

The fungicidal composition optionally further comprises one or more polymeric stabilizer. The suitable polymeric stabilizers that may be used include, but are not limited to, polypropylene, polyisobutylene, polyisoprene, copolymers of monoolefins and diolefins, polyacrylates, polystyrene, polyvinyl acetate, polyurethanes or polyamides. Suitable stabilizers are known in the art and commercially available.

The surfactants and polymeric stabilizers mentioned above are generally believed to impart stability to the composition, in turn allowing the composition to be formulated, stored, transported and applied.

Suitable anti-foams include all substances which can normally be used for this purpose in agrochemical compositions. Suitable anti-foam agents are known in the art and are available commercially. Particularly preferred antifoam agents are mixtures of polydimethylsiloxanes and perfluoroalkylphosphonic acids, such as the silicone anti-foam agents available from GE or Compton.

Suitable organic solvents are selected from all customary organic solvents which thoroughly dissolve the active compounds employed. Again, suitable organic solvents for the active components (A) and (B) are known in the art. The following may be mentioned as being preferred: N-methyl pyrrolidone, N-octyl pyrrolidone, cyclohexyl-1-pyrrolidone; or SOLVESSO™200, a mixture of paraffinic, isoparaffinic, cycloparaffinic and aromatic hydrocarbons. Suitable solvents are commercially available.

Suitable preservatives include all substances which can normally be used for this purpose in agrochemical compositions of this type and again are well known in the art. Suitable examples that may be mentioned include PREVENTOL® (from Bayer AG) and PROXEL® (from Bayer AG).

Suitable antioxidants are all substances which can normally be used for this purpose in agrochemical compositions, as is known in the art. Preference is given to butylated hydroxytoluene.

Suitable thickeners include all substances which can normally be used for this purpose in agrochemical compositions. For example xanthan gum, PVOH, cellulose and its derivatives, clay hydrated silicates, magnesium aluminum silicates or a mixture thereof. Again, such thickeners are known in the art and available commercially.

The fungicidal composition may further comprise one or more solid adherents. Such adherents are known in the art and available commercially. They include organic adhesives, including tackifiers, such as celluloses of substituted celluloses, natural and synthetic polymers in the form of powders, granules, or lattices, and inorganic adhesives such as gypsum, silica, or cement.

In addition, depending upon the formulation, the composition according to the invention may also comprise water.

In some embodiments, compositions according to the present invention comprise the following combinations of components:

(A) azoxystrobin, (B) cyproconazole;
(A) azoxystrobin, (B) difenoconazole;
(A) azoxystrobin, (B) flutriafol;
(A) azoxystrobin, (B) metconazole;
(A) azoxystrobin, (B) propiconazole;
(A) azoxystrobin, (B) tebuconazole;
(A) picoxystrobin, (B) cyproconazole;
(A) picoxystrobin, (B) difenoconazole;
(A) picoxystrobin, (B) flutriafol;
(A) picoxystrobin, (B) metconazole;
(A) picoxystrobin, (B) propiconazole;
(A) picoxystrobin, (B) tebuconazole;
(A) pyraclostrobin, (B) cyproconazole;
(A) pyraclostrobin, (B) difenoconazole;
(A) pyraclostrobin, (B) flutriafol;
(A) pyraclostrobin, (B) metconazole;
(A) pyraclostrobin, (B) propiconazole; or
(A) pyraclostrobin, (B) tebuconazole.

According to a preferred embodiment, the composition according to the present invention comprises components (A) azoxystrobin and (B) cyproconazole.

Each of the compositions can be used in the agricultural sector and related fields of use for increasing the yield of plants which are susceptible to fungal diseases caused by fungal pathogens.

Each of the compositions is effective in increasing the yield of plants which are susceptible to fungal diseases caused by fungal pathogens, for example, but not limited to:

*Glomerella gossypii* and *Colletotrichum gossypii* [anamorph] (anthracnose); *Ramularia gossypii* (areolate mildew); *Alternaria macrospora*, *Alternaria alternate* and *Cercospora gossypina* (Leaf spot); *Puccinia schedonnardii* (Cotton rust) on cotton;

*Colletotrichum gloeosporioides*, *Glomerella cingulata* [teleomorph] and *Colletotrichum kahawae* (anthracnose); *Cercospora coffeicola* (Brown eye spot); *Hemileia vastatrix* (Rust (orange or leaf rust); *Hemileia coffeicola* (powdery or grey rust) on coffee;

*Ceratocystis adiposa* (Black rot); *Cercospora atrofiliformis* (Black stripe); *Cercospora longipes* (Brown spot); *Puccinia melanocephala* (Rust); *Puccinia kuehnii* (Rust, orange) on sugarcane;

*Alternaria alternata*, *Alternaria helianthi*, *Alternaria helianthicola*, *Alternaria leucanthemi*, *Alternaria tenuissima* and *Alternaria zinniae* (*Alternaria* leaf blight, stem spot and head rot); *Puccinia helianthi* and *Puccinia xanthii* (Rust) on sunflower;

*Colletotrichum graminicola*, *Glomerella graminicola* [teleomorph], *Glomerella tucumanensis* and *Glomerella falcatum* [anamorph] (Anthracnose leaf blight and Anthracnose stalk rot); *Cercospora sorghi* and *Cercospora zeae-maydis* (Gray leaf spot and *Cercospora* leaf spot); *Puccinia sorghi* (Rust); *Puccinia polysora* (Rust, southern corn) on corn.

*Colletotrichum truncatum*, *Colletotrichum dematium* f. *truncatum*, *Glomerella glycines*, *Colletotrichum destructivum* [anamorph] (Anthracnose); *Mycoleptodiscus terrestris* (*Mycoleptodiscus* root rot); *Cercospora kikuchii* (Purple seed stain); *Phakopsora pachyrhizi* (Rust); *Diaporthe phaseolorum*, *Diaporthe phaseolorum* var. *caulivora*, *Phomopsis phaseoli* [anamorph] (Stem canker) on soybean; and

*Puccinia triticina* and *Puccinia tritici-duri* (Leaf rust); *Puccinia graminis* (Stem rust); *Puccinia striiformis* (Stripe rust) on wheat.

The fungal disease to be treated and/or prevented may be selected from the group comprising rust, anthracnose and stem canker. In certain embodiments, the fungal disease is soybean rust.

The composition exhibits surprisingly high activity in increasing the yield of a plant which is susceptible to fungal diseases caused by fungal pathogens, particularly *Colletotrichum* spp., *Alternaria* spp., *Cercospora* spp., *Puccinia* spp, *Mycoleptodiscus terrestris*, *Phakopsora pachyrhizi*, *Diaporthe phaseolorum*, *Diaporthe phaseolorum* var. *caulivora* and *Phomopsis phaseoli* [anamorph]. In some embodiments, the composition in the present invention can increase the yield of soybean which is susceptible to fungal diseases caused by *Phakopsora pachyrhizi*.

The composition is suitable for plants of the crops: cereals (wheat, barley, rye, oats, corn, rice, sorghum, triticale and related crops); beet (sugar beet and fodder beet); fruit, such as pomes, stone fruit and soft fruit, such as apples, pears, plums, peaches, almonds, cherries, and berries, for example strawberries, raspberries and blackberries; leguminous plants (beans, lentils, peas, soybeans); oil plants (rape, mustard, sunflowers); cucurbitaceae (marrows, cucumbers, melons); fibre plants (cotton, flax, hemp, jute); citrus fruit, such as oranges, lemons, grapefruit and mandarins; vegetables (spinach, lettuce, asparagus, cabbages, carrots, onions, tomatoes, potatoes, paprika); as well as ornamentals (flowers, shrubs, broad-leaved trees and evergreens, such as conifers). In some embodiments, the composition of the present invention is applied on cotton, coffee, sugar cane, sunflower, corn, soybean and wheat. In certain embodiments, the composition is applied on cotton, coffee, sugar cane, sunflower, corn and soybean. In some embodiments, the composition is applied on soybean. Each of the compositions can be applied to the foliage of the plant.

The composition may contain or be mixed with other pesticides, such as other fungicides, insecticides and nematicides, growth factor and fertilizers.

The rates of application (use) of the composition may vary, for example, according to type of use, type of crop, the specific active compounds in the combination, type of plants, but is such that the active compounds in the combination in an effective amount to provide the desired action (such as disease or pest control). The application rate of the composition for a given set of conditions can readily be determined by trials.

The effective amount of the composition can be 50-600 g/ha, particularly 50-150 g/ha, 100-500 g/ha, 250-500 g/ha, 250-300 g/ha or 300-500 g/ha. In some embodiments, the effective amount of the composition is 50-150 g/ha. In certain embodiments, the effective amount of the composition is 250-500 g/ha. Preferred application rates may be 10-500 g/ha of component (A); and 5-350 g/ha of component (B).

The components (A) and (B), and any other pesticides, may be applied and used in pure form, as a solid active compound, for example, in a specific particle size, or preferably together with at least one of the auxiliary or adjuvant components, as is customary in formulation technology, such as extenders, for example solvents or solid carriers, or surface-active compounds (surfactants), as described in more detail above. Generally, the components (A) and (B) are in the form of a formulation composition with one or more of the aforementioned customary formulation auxiliaries.

As described above, embodiments of the present invention also provide a method of increasing the yield of a plant in which the plant, one or more parts thereof (such as leaves or seeds), or surrounding is treated with each of the active components (A) and (B). The active components (A) and (B) can be applied to the surrounding where control is desired either simultaneously or in succession at short intervals, for example on the same day. The active components (A) and (B) may be applied in any suitable form, as described above. Typically, the active components will be applied as formulations, that is compositions comprising one or more of the active components together with further carriers, surfactants or other application-promoting adjuvants customarily employed in formulation technology.

The components (A) and (B) may be applied to the plant, one or more parts thereof (such as leaves or seeds), or surrounding in any order. Each compound may be applied just once or a plurality of times. Preferably, each of the components (A) and (B) are applied a plurality of times, in particular from 2 to 5 times, more preferably 3 times.

The components (A) and (B) may be applied in the above amounts relative to each other, in order to obtain the enhanced or synergistic effect of the combination. In particular, the relative amounts of the compounds to be applied to the plant, one or more parts thereof (such as leaves or seeds), or surrounding are as hereinbefore described, with the ratio of the components (A) and (B) preferably being in the range of from 25:1 to 1:25, 20:1 to 1:20 and 15:1 to 1:15, more preferably from 10:1 to 1:10, 5:1 to 1:5 or 2.5:1 to 1:2.5.

In the event compounds (A) and (B) are applied simultaneously, they may be applied as a composition containing components (A) and (B), in which case components (A) and (B) can be obtained from a separate formulation source and mixed together (known as a tank-mix, ready-to-apply, spray broth, or slurry), optionally with other pesticides, or components (A) and (B) can be obtained as a single formulation mixture source (known as a pre-mix, concentrate, formulated compound (or product)), and optionally mixed together with other pesticides.

In some embodiments, the combination of the components (A) and (B) applied by way of the method of the present invention is applied as a composition, as hereinbefore described. Accordingly, embodiments of the present invention relates to a composition comprising as active ingredients (AI), components (A) and (B), and optionally other pesticides, and optionally one or more customary formulation auxiliaries; which may be in the form of a tank-mix or pre-mix composition.

Generally, a tank-mix formulation comprises 0.1 to 20%, especially 0.1 to 15%, active compounds, and 99.9 to 80%, especially 99.9 to 85%, of one or more solid or liquid auxiliaries (including for example, a solvent such as water), where the auxiliaries can be surfactant in an amount of 0 to 20%, especially 0.1 to 15%, based on the tank-mix formulation.

Typically, a pre-mix formulation comprises 0.1 to 99.9%, especially 1 to 95%, active compounds, and 99.9 to 0.1%, especially 99 to 5%, of a solid or liquid adjuvant (including, for example, a solvent such as water), where the auxiliaries can be a surfactant in an amount of 0 to 50%, especially 0.5 to 40%, based on the pre-mix formulation.

The composition may be applied to the foliage of the plant or to the surrounding.

In a preferred embodiment of the invention, the combinations of:
(A) azoxystrobin, (B) cyproconazole;
(A) azoxystrobin, (B) difenoconazole;
(A) azoxystrobin, (B) flutriafol;
(A) azoxystrobin, (B) metconazole;
(A) azoxystrobin, (B) propiconazole;
(A) azoxystrobin, (B) tebuconazole;
(A) picoxystrobin, (B) cyproconazole;
(A) picoxystrobin, (B) difenoconazole;
(A) picoxystrobin, (B) flutriafol;
(A) picoxystrobin, (B) metconazole;
(A) picoxystrobin, (B) propiconazole;
(A) picoxystrobin, (B) tebuconazole;
(A) pyraclostrobin, (B) cyproconazole;
(A) pyraclostrobin, (B) difenoconazole;
(A) pyraclostrobin, (B) flutriafol;
(A) pyraclostrobin, (B) metconazole;
(A) pyraclostrobin, (B) propiconazole; and
(A) pyraclostrobin, (B) tebuconazole
are each provided in the form of a pre-mix composition (or mixture).

According to embodiments of the invention each of the components (A) and (B) in the combination independently may be one or more than one active compounds. In a further particular embodiment, the composition of the invention comprises, in addition to the combination of the active components, one or more further active compounds, and optionally suitable adjuvant and/or auxiliary.

Examples of formulation types for pre-mix compositions are:

water-soluble concentrate (SL), an emulstifiable concentrate (EC), an emulsion (EW), a micro-emulsion (ME), a suspension concentrates (SC), an oil-based suspension concentrates (OD), a flowable suspension (FS), a water-dispersible granule (WG), water-soluble granule (SG), a water-dispersible powder (WP), a water soluble powder (SP), a granule (GR), an encapsulated granule (CG), a fine granule (FG), a macrogranule (GG), an aqueous suspo-emulsion (SE), capsule suspension (CS) and a microgranule (MG).

Using such formulations, either straight (that is undiluted) or diluted with a suitable solvent, especially water, plants and loci can be treated and protected against damage, for example by pathogen(s), by spraying, pouring or immersing. In some embodiments, the composition is suspension concentrate.

In some embodiments, a method of increasing the yield of soybean comprising steps:
(1) applying soybeans which is susceptible to soybean rust caused by *Phakopsora pachyrhizi* with 250-500 g/ha of a composition comprising components of (A) azoxystrobin and (B) cyproconazole having a weight ratio of components (A) to (B) in 2.5:1; and
(2) growing soybean to increase the yield of soybean by at least about 0.5%.

The compositions according to embodiments of the invention are distinguished by the fact that they are especially well tolerated by plants and are environmentally friendly.

Each composition is especially advantageous for the treatment of plants.

The following examples are given by way of illustration and not by way of limitation of the invention.

FORMULATION EXAMPLES

Example 1

An aqueous suspension concentrate was prepared having the following composition:

| | |
|---|---|
| Azoxystrobin | 200 g |
| Cyproconazole | 80 g |
| Propylene glycol | 200 g |
| Tristyrylphenol ethoxylates | 100 g |
| Sodium lignosulfonate | 200 g |
| Carboxymethylcellulose | 20 g |
| Silicone oil (in the form of a 75% emulsion in water) | 20 g |
| Water | Balance to 1 L |

The finely ground azoxystrobin and cyproconazole were intimately mixed with the adjuvants, giving a suspension concentrate from which suspensions of any desired dilution could be obtained by dilution with water. As an alternative, a suspension of azoxystrobin and cyproconazole and auxiliaries (including water) was wet milled with a bead-mill to achieve a stable formulation with appropriate treatment characteristics.

Example 2

An aqueous suspension concentrate was prepared having the following composition:

| | |
|---|---|
| Picoxystrobin | 10 g |
| Cypoconazole | 500 g |
| Propylene glycol | 100 g |
| Tristyrylphenol ethoxylates | 50 g |
| Sodium lignosulfonate | 100 g |
| Carboxymethylcellulose | 10 g |
| Silicone oil (in the form of a 75% emulsion in water) | 10 g |
| Water | Balance to 1 L |

The finely ground picoxystrobin and cypoconazole were intimately mixed with the auxiliaries, giving a suspension concentrate from which suspensions of any desired dilution could be obtained by dilution with water. As an alternative, a suspension of picoxystrobin and cypoconazole and auxiliaries (including water) was wet milled with a bead-mill to achieve a stable formulation and with the appropriate treatment characteristics.

Example 3

An aqueous suspension concentrate was prepared having the following composition:

| | |
|---|---|
| Pyraclostrobin | 500 g |
| Cyproconazole | 10 g |
| Propylene glycol | 100 g |
| Tristyrylphenol ethoxylates | 50 g |
| Sodium lignosulfonate | 100 g |
| Carboxymethylcellulose | 10 g |
| Silicone oil (in the form of a 75% emulsion in water) | 10 g |
| Water | Balance to 1 L |

The finely ground pyraclostrobin and cyproconazole were intimately mixed with the auxiliaries, giving a suspension concentrate from which suspensions of any desired dilution could be obtained by dilution with water. As an alternative, a suspension of pyraclostrobin and cyproconazole and auxiliaries (including water) was wet milled with a bead-mill to achieve a stable formulation and with the appropriate treatment characteristics.

Example 4

An emulsifiable concentrate was prepared having the following composition:

| | |
|---|---|
| Azoxystrobin | 80 g |
| Cypoconazole | 200 g |
| Propylene glycol | 100 g |
| Tristyrylphenol ethoxylates | 50 g |
| Sodium lignosulfonate | 100 g |
| Carboxymethylcellulose | 10 g |
| Silicone oil (in the form of a 75% emulsion in water) | 10 g |
| N-methylpyrrolidone | Balance to 1 L |

Example 5

An emulsion in water was prepared having the following composition:

| | |
|---|---|
| Picoxystrobin | 50 g |
| Cypoconazole | 250 g |
| Propylene glycol | 100 g |
| Tristyrylphenol ethoxylates | 50 g |
| Sodium lignosulfonate | 100 g |
| Carboxymethylcellulose | 10 g |
| Silicone oil (in the form of a 75% emulsion in water) | 10 g |
| N-methylpyrrolidone | 300 g |
| Water | Balance to 1 L |

Example 6

A suspo-emulsion was prepared having the following composition:

| | |
|---|---|
| Azoxystrobin | 200 g |
| Cyproconazole | 40 g |
| N-methylpyrrolidone | 150 g |
| Alkamuls OR/36 | 45 g |
| Polyerethanes | 30 g |
| TERSPERSE ® 2500 | 3.75 g |
| SOPROPHOR ® FLK | 15 g |
| Propylene glycol | 150 g |
| 2% xanthan gum | 112.5 g |
| Silicone oil (in the form of a 75% emulsion in water) | 15 g |
| Water | Balance to 1 L |

Cyproconazole was mixed with N-methyl pyrrolidone and the emulsifiers OR/36 and polymeric stabilizer polyurethanes to get an oil phase. The finely ground azoxystrobin was intimately mixed with the other auxiliaries (including water), giving a water phase. As an alternative, a suspension of the azoxystrobin and cyproconazole and auxiliaries (including water) was wet milled with a bead-mill to achieve a water phase. The oil phase was added to water phase under continuous agitation for an optimum amount of time.

Example 7

A suspo-emulsion was prepared having the following composition:

| | |
|---|---|
| Pyraclostrobin | 120 g |
| Difenoconazole | 12 g |
| N-methylpyrrolidone | 100 g |
| Alkamuls OR/36 | 30 g |
| Polyerethanes | 20 g |
| TERSPERSE ® 2500 | 2.5 g |
| SOPROPHOR ® FLK | 10 g |
| Propyleneglycol | 100 g |
| 2% xanthan gum | 75 g |
| Silicone oil (in the form of a 75% emulsion in water) | 10 g |
| Water | Balance to 1 L |

Difenconazole was mixed with N-methyl pyrrolidone and the emulsifiers OR/36 and polymeric stabilizer polyurethanes to get an oil phase. The finely ground pyraclostrobin was intimately mixed with the other auxiliaries (including water), giving a water phase. As an alternative, a suspension of the pyraclostrobin and difenoconazole and auxiliaries (including water) was wet milled with a bead-mill to achieve a water phase. The oil phase was added to water phase under continuous agitation for an optimum amount of time.

Example 8

An oil-based suspension concentrate was prepared having the following composition:

| | |
|---|---|
| Azoxystrobin | 250 g |
| Cyproconazole | 25 g |
| Propylene glycol | 150 g |
| Tristyrylphenol ethoxylates | 75 g |
| Sodium lignosulfonate | 150 g |
| Carboxymethylcellulose | 15 g |
| Silicone oil (in the form of a 75% emulsion in water) | 15 g |
| Vegetable oil | Balance to 1 L |

The finely ground azoxystrobin and cyproconazole were intimately mixed with the auxiliaries, giving a suspension concentrate from which suspensions of any desired dilution could be obtained by dilution with water.

Example 9

A flowable suspension was prepared having the following composition:

| | |
|---|---|
| Azoxystrobin | 200 g |
| Difenoconazole | 10 g |
| $C_{16}$-$C_{18}$ fatty alcohol polyoxyethylene ether (25EO) | 10 g |
| Alkyl polysaccharide | 20 g |
| Hydroxyethyl cellulose | 12 g |
| 1,2-Benzisothiazolin-3-one | 6 g |
| Red pigment | 40 g |
| Propylene glycol | 100 g |
| Silicon oil | 4 g |
| Water | Balance to 1 L |

The finely ground azoxystrobin and difenoconazole were grounded with the auxiliaries in a sand mill, giving a flowable suspension with particle size of approximately 3 mm.

Example 10

A water-dispersible granule was prepared having the following composition:

| | |
|---|---|
| Azoxystrobin | 10 g |
| Cyproconazole | 200 g |
| $C_{12}$-$C_{14}$ fatty alcohol polyoxyethylene ether (20EO) | 100 g |
| Sodium lauryl benzenesulfonate | 60 g |
| Sucrose | Balance to 1000 g |

With the water-dispersible granule, an aqueous suspension of required concentration was obtained through dilution of the water dispersible granule with an appropriate amount of water.

Example 11

A water-dispersible granule was prepared having the following composition:

| | |
|---|---|
| Azoxystrobin | 62 g |
| Propiconazole | 104 g |
| $C_{12}$-$C_{14}$ fatty alcohol polyoxyethylene ether (20EO) | 25 g |
| Sodium lauryl benzenesulfonate | 15 g |
| Sucrose | Balance to 1000 g |

With the water-dispersible granule, an aqueous suspension of required concentration was obtained through dilution of the water dispersible granule with an appropriate amount of water.

Biological Examples

Field Test 1—Percentage Change of Yield on Soybean

Young soybean plants were sprayed with a conidial suspension of white mold (*Phakopsora pachyrhizi*), and incubated at 20° C. and 100% relative atmospheric humidity for 48 hours. Then they were sprayed with Formulations Examples set out above. The application rate was 100 g AI/ha. After staying in a greenhouse at 15° C. and 80% relative atmospheric humidity for 15 days, yield of soybean was assessed. Dry weights of the plants were determined. Percentage change of yield is calculated by:

(Total weight of seed$_{test}$−Total weight of seed$_{control}$)/Total weight of seed$_{control}$×100%

The results of the assessment are set out in Table A below

TABLE A

| Test | Application rate of components A + B (g AI/ha) | Number of pod per plants (average) | Total weight of seed (kg/ha) | Percentage change of yield (compared with the control experiment) |
|---|---|---|---|---|
| Untreated | 0 + 0 | 18 | 1136 | — |
| Azoxystrobin 250 g/L SC AMISTAR ® | 250 + 0 | 30 | 1523.4 | 34.1 |
| Pyraclostrobin 250 g/L SC HEADLINE ® | 250 + 0 | 28 | 1439.3 | 26.7 |
| Picoxystrobin 250 g/L SC ACANTO ® | 250 + 0 | 27 | 1392.7 | 22.6 |
| Cyproconazole 100 g/L SL ALTO ® | 0 + 100 | 31 | 1521.1 | 33.9 |
| Propiconazole 250 g/L EC 4 FARMERS ® | 0 + 250 | 30 | 1479.1 | 30.2 |
| Difenoconazole 250 g/L SCORE ® | 0 + 250 | 30 | 1476.8 | 30 |
| Example 1 | 71.43 + 28.57 | 65 | 1993 | 75.4 |
| Example 2 | 1.96 + 98.04 | 55 | 1785 | 57.1 |
| Example 3 | 98.04 + 1.96 | 58 | 1865 | 64.2 |
| Example 4 | 28.57 + 71.43 | 61 | 2013 | 77.2 |
| Example 5 | 16.67 + 83.33 | 63 | 2060 | 81.3 |
| Example 6 | 83.33 + 16.67 | 58 | 1860 | 63.7 |
| Example 7 | 90.91 + 9.09 | 57 | 1872 | 64.8 |
| Example 8 | 90.91 + 9.09 | 59 | 1964 | 72.9 |
| Example 9 | 95.24 + 4.76 | 60 | 2015 | 77.4 |
| Example 10 | 4.76 + 95.24 | 62 | 2038 | 79.4 |
| Example 11 | 37.35 + 62.65 | 61 | 2025 | 78.3 |

Field Test 2—Percentage Change of Yield on Cotton

Young cotton plants were sprayed with a conidial suspension of white mold (*Puccinia schedonnardii*), and incubated at 20° C. and 100% relative atmospheric humidity for 48 hours. Then they were sprayed with Formulations Examples set out above. The application rate was 112 g AI/ha. After staying in a greenhouse at 15° C. and 80% relative atmospheric humidity for 15 days, yield of cotton was assessed. Number of bolls and total weight of bolls were determined. Average weight of bolls in gram is calculated by:

Average weight of bolls (g)=Total weight of boll (g)/Number of bolls

The results of the assessment are set out in Table B below.

TABLE B

| Test | Application rate of components A + B (g AI/ha) | Total weight of bolls (g) | Average weight of bolls (g) |
|---|---|---|---|
| Untreated | 0 + 0 | 70.2 | 3.51 |
| Azoxystrobin 250 g/L SC AMISTAR ® | 250 + 0 | 121 | 4.32 |
| Pyraclostrobin 250 g/L SC HEADLINE ® | 250 + 0 | 97.3 | 3.98 |
| Picoxystrobin 250 g/L SC ACANTO ® | 250 + 0 | 103.2 | 3.97 |
| Cyproconazole 100 g/L SL ALTO ® | 0 + 100 | 119.3 | 4.42 |
| Propiconazole 250 g/L EC 4 FARMERS 0 | 0 + 250 | 104.8 | 4.03 |
| Difenoconazole 250 g/L SCORE ® | 0 + 250 | 103.5 | 3.98 |
| Example 1 | 80.00 + 32.00 | 264.8 | 6.62 |
| Example 2 | 2.20 + 109.80 | 231.4 | 6.09 |
| Example 3 | 109.80 + 2.20 | 220.5 | 5.96 |
| Example 4 | 32.00 + 80.00 | 240.6 | 6.33 |
| Example 5 | 18.67 + 93.33 | 244.0 | 6.10 |
| Example 6 | 93.33 + 18.67 | 258.6 | 6.63 |
| Example 7 | 101.81 + 10.18 | 248.5 | 6.54 |
| Example 8 | 101.81 + 10.18 | 239.4 | 6.47 |
| Example 9 | 106.67 + 5.33 | 248.5 | 6.54 |
| Example 10 | 5.33 + 106.67 | 253.5 | 6.50 |
| Example 11 | 41.83 + 70.17 | 247.3 | 6.34 |

Field Test 3—Sugarcane

Young sugarcane plants were sprayed with a conidial suspension of white mold (*Cercospora longipes*), and incubated at 20° C. and 100% relative atmospheric humidity for 48 hours. Then they were sprayed with Formulations Examples set out above. The application rate was 140 g AI/ha. After staying in a greenhouse at 15° C. and 80% relative atmospheric humidity for 15 days, yield of sugarcane was assessed. Dry weights of the plants were determined. Percentage change of yield is calculated by:

(Dry weight$_{test}$−Dry weight$_{control}$)/Dry weight$_{control}$×100%

The results of the assessment are set out in Table C below.

TABLE C

| Test | Application rate of components A + B (g AI/ha) | Percentage change of yield (compared with the control experiment) |
|---|---|---|
| Untreated | 0 + 0 | — |
| Azoxystrobin 250 g/L SC AMISTAR ® | 250 + 0 | 78.3 |
| Pyraclostrobin 250 g/L SC HEADLINE ® | 250 + 0 | 71.2 |
| Picoxystrobin 250 g/L SC ACANTO ® | 250 + 0 | 75.6 |
| Cyproconazole 100 g/L SL ALTO ® | 0 + 100 | 77.4 |
| Propiconazole 250 g/L EC 4 FARMERS ® | 0 + 250 | 79.2 |
| Difenoconazole 250 g/L SCORE ® | 0 + 250 | 70.1 |
| Example 1 | 100 + 40 | 187.5 |
| Example 2 | 2.75 + 137.25 | 193.2 |
| Example 3 | 137.25 + 2.75 | 186.3 |
| Example 4 | 40 + 100 | 204.5 |
| Example 5 | 23.33 + 116.67 | 210.2 |
| Example 6 | 116.67 + 23.33 | 198.4 |
| Example 7 | 127.27 + 12.73 | 194.3 |
| Example 8 | 127.27 + 12.73 | 200.4 |
| Example 9 | 133.33 + 6.67 | 209.2 |
| Example 10 | 6.67 + 133.33 | 210.8 |
| Example 11 | 52.29 + 87.71 | 186.4 |

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

The invention claimed is:

1. A method of increasing the yield of a plant comprising steps:
   (1) applying to a plant which is susceptible to fungal diseases caused by fungal pathogens an effective amount of a composition comprising components:
   (A) azoxystrobin, and (B) difenoconazole; and
   (2) growing the plant applied with said composition including both of the azoxystrobin and the difenoconazole to increase the yield of the plant at least 50% relative to a plant that is not applied with said composition.

2. The method according to claim 1, wherein the plant is selected from the group consisting of cotton, coffee, sugar cane, sunflower, corn, soybean and wheat.

3. The method according to claim 1, wherein the effective amount of the composition is 50-600 g/ha.

4. The method according to claim 1, wherein the component (A) is between 5% to 95% by weight of the composition.

5. The method according to claim 1, wherein the component (B) is between 1% and 70% by weight of the composition.

6. The method according to claim 1, wherein the components (A) and (B) are present in amounts such that the weight ratio of the components is from 25:1 to 1:25.

7. The method according to claim 1, wherein the components (A) and (B) are applied simultaneously.

8. The method according to claim 1, wherein the step (1) comprises applying the composition to the foliage of the plant.

9. The method according to claim 1, wherein the fungal disease is selected from rust, anthracnose and stem canker.

10. The method according to claim 1, wherein the fungal pathogens are selected from the group consisting of *Colletotrichum* spp., *Alternaria* spp., *Cercospora* spp., *Puccinia* spp, *Mycoleptodiscus terrestris, Phakopsora pachyrhizi, Diaporthe phaseolorum, Diaporthe phaseolorum* var. *caulivora* and *Phomopsis phaseoli* [*anamorph*] or a combination thereof.

11. The method according to claim 1, wherein the composition is a granule formulation, aqueous suspension concentrate, water-dispersible granule formulation, water-soluble granule formulation, water-dispersible powder formulation, water-soluble powder formulation, or a flowable suspension formulation.

12. The method according to claim 2, wherein the plant is soybean.

13. The method according to claim 9, wherein the fungal disease is soybean rust.

14. The method according to claim 1, wherein the increasing of the yield is at least about 0.5%.

15. The method according to claim 1, wherein the effective amount of the composition is 300-500 g/ha.

16. The method according to claim 1, wherein the component (A) is between 15% to 50% by weight of the composition.

17. The method according to claim 1, wherein the component (B) is from 5% to 25% by weight of the composition.

18. The method according to claim 1, wherein the components (A) and (B) are present in amounts such that the weight ratio of the components is from 2.5:1 to 1:2.5.

* * * * *